United States Patent [19]
van de Winkel

[11] Patent Number: 6,146,837
[45] Date of Patent: Nov. 14, 2000

[54] CYANIDIN COMPOSITIONS AND THERAPEUTIC AND DIAGNOSTIC USES THEREFOR

[75] Inventor: Jan G. J. van de Winkel, Odijk, Netherlands

[73] Assignee: Medarex, Inc., Annandale, N.J.

[21] Appl. No.: 09/197,683

[22] Filed: Nov. 23, 1998

Related U.S. Application Data

[62] Division of application No. 08/709,411, Sep. 6, 1996.

[51] Int. Cl.[7] .................. C07D 209/02; C07D 209/56; C01N 33/53
[52] U.S. Cl. .................. 435/7.1; 548/427; 548/455; 530/370; 530/387.1; 530/388.22; 530/388.9; 530/388.7
[58] Field of Search .................. 435/7.1; 548/427, 548/455; 530/370, 387.1, 388.22, 388.9, 388.7

[56] References Cited

U.S. PATENT DOCUMENTS

| | | |
|---|---|---|
| 4,857,474 | 8/1989 | Waterbury et al. . |
| 4,981,977 | 1/1991 | Southwick et al. . |
| 5,137,809 | 8/1992 | Loken et al. . |
| 5,234,816 | 8/1993 | Terstappen . |
| 5,256,542 | 10/1993 | Chang . |
| 5,268,486 | 12/1993 | Waggoner et al. . |

FOREIGN PATENT DOCUMENTS

| | | |
|---|---|---|
| 0 629 703 | 12/1994 | European Pat. Off. . |
| 0 708 336 | 4/1996 | European Pat. Off. . |

OTHER PUBLICATIONS

Ansari, M.O. et al., "Flourochrome Specific PE/CY5 Tandem (Tricolor) Staining is Sensitive and Specific for Acute promyelocytic Leukemia (AML–FAB M3)", *Clinical Cytometry Society:Abstracts* p. 83 (1994).
Capsoni, Franco et al., "IL–10 up–regulates human monocyte phagocytosis in the presence of IL–4 and IFN–γ", *Journal of Leukocyte Biology*, vol. 58 pp. 351–358 (1995).
Ceuppens, J. et al, "Defect in the Membrane Expression of High Affinity 72–kD Fc γ Receptors on Phagocytic Cells in Four Healthy Subjects", *Journal of Clinical Investigation*, vol. 82 pp. 571–578 (1988).
Davis, B.H. et al. "Neutrophil CD64 expression: Potential diagnostic indicator of acute inflammation and therapeutic monitor of interferon–γ therapy", *Laboratory Hematology*, 1 pp. 3–12 (1995).
Dutton, G. "New Moves Attempt to Boost Research on Nutraceuticals", Genetic Engineering News, vol. 16 No. 11 pp. 1,23,27 (1996).
Ericson, S.G. et al. "Monoclonal antibody 197 (anti–FcγRI) infusion in a patient with immune thrombocytopenia purpura (ITP) results in down–modulation of FcγRI on circulating monocytes", *British Journal of Haematology*, vol. 92 pp. 718–724 (1996).
Ernst, L. et al. "Cyanine Dye Labeling Reagents for Sulfhydryl Groups", *Cytometry*, vol. 10 pp. 3–10 (1989).

Guyre, P. et al. "Recombinant Immune Interferon Increases Immunoglobulin G Fc Receptors on Cultured Human Mononuclear Phagocytes", *Journal of Clinical Investigation*, vol. 72 pp. 393–397 (1983).
Guyre, P. "Monocytes and Polymorphonuclear Neutrophils of Patients with *Streptococcal pharyngitis* Express Increased Numbers of Type 1 IgG Fc Receptors", *Journal of Clinical Investigation*, vol. 86 pp. 1892–1896 (1990).
Howard, M.R. et al. "Variable detection of myeloid antigens in childhood acute lymphoblastic leukaemia", *Journal of Clinical Pathology*, vol. 47 pp. 1006–1009 (1994).
Immunotech–Coulter Catalog, Cytometry Monoclonal Reagent Guide, pp. 3 (1995).
Krause, D. et al. "CD34: Structure, Biology, and Clinical Utility", *Blood*, vol. 87 No. 1 pp. 1–13 (1996).
Kronick, M. "The use of phycobiliproteins as fluorescent labels in immunoassay", *Journal of Immunological Methods*, vol. 92 pp. 1–13 (1986).
Lohmeyer, J. et al. "Multiparameter flow cytometric analysis of inflammatory cells contained in bronchoalveolar lavage fluid", *Journal of Immunological Methods*, vol. 172 pp. 59–70 (1994).
Majima, T. et al. "Unusual Expression of IgG Fc Receptors on Peripheral Granulocytes from Patients with Leukocyte Adhesion Deficiency (CD11/CD18 Deficiency)", *Journal of Immunology*, vol. 145 No. 6 pp. 1694–1699 (1990).
Morton, H. C. et al. "Functional Association between the Human Myeloid Immunoglobin A Fc Receptor (CD89) and Fc γ Chain", *Journal of Biological Chemistry*, vol. 270 pp. 29781–29787 (1995).
Mujumdar, R. et al. "Cyanine Dye Labeling Reagents:Sulfoindocyanine Succinimidyl Esters", *Bioconjugate Chemistry*, vol. 4 No. 2 pp. 105–111 (1993).
Mujumdar, S. et al. "Cyanine–Labeling Reagents: Sulfobenzindocyanine Succinimidyl Esters", *Bioconjugate Chemistry*, vol. 7 No. 3 pp. 356–362 (1996).
Ravetch, J. et al. "Fc Receptors", *Annual Review Immunology*, vol. 9 pp. 457–492 (1991).
Repp, R. et al. "Neutrophils Express the High Affinity Receptor for IgG (FcγRI, CD64) After In Vivo Application of Recombinant Human Granulocyte Colony–Stimulating Factor", *Blood*, vol. 78 No. 4 pp. 885–889 (1991).
Southwick, P. et al. "Cyanine Dye Labeling Reagents— Carboxymethylindocyanine Succinimidyl Esters", *Cytometry*, vol. 11 pp. 418–430 (1990).
Valerius, T. et al. "Involvement of the High–Affinity Receptor for IgG (FcγRI; CD64) in Enhanced Tumor Cell Cytotoxicity of Neutrophils during Granulocyte Colony–Stimulating Factor Therapy", *Blood*, vol. 82 No. 3 pp. 931–939 (1993).

(List continued on next page.)

*Primary Examiner*—Christina Y. Chan
*Assistant Examiner*—Martha Lubet
*Attorney, Agent, or Firm*—Lahive & Cockfield, LLP; Jane E. Remillard, Esquire; Jeanne M. DiGiorgio, Esq.

[57] ABSTRACT

Compositions comprising cyanidin reagents for binding to FcγRI receptors, and methods and kits for use therefor are provided.

14 Claims, 2 Drawing Sheets

OTHER PUBLICATIONS

Van de Winkel, J.G.J. et al."Human IgG Fc receptor heterogeneity: molecular aspects and clinical implications", *Immunology Today*, vol. 14 No. 5 pp. 215–221 (1993).

Van den Herik–Oudijk, I. et al."Identification of Signaling Motifs within Human FcγRIIa and FcγRIIb Isoforms", *Blood*, vol. 85 No. 8 pp. 2202–2211 (1995).

Van Vugt, M.J. et al."FcR γ–Chain is Essential for both Surface Expression and Function of Human FcγRI (CD674) In Vivo", *Blood*, vol. 87 No. 9 pp. 3593–3599 (1996).

Repp, R. et al."Neutrophils Express the High Affinity Receptor for IgG (FcγRI, CD64) After In Vivo Application of Recombinant Human Granulocyte Colony–Stimulating Factor", *Blood*, vol. 78 No. 4 pp. 885–889 (1991).

Van Vugt, M. et al., "Binding of PE–Cy5 Conjugates to the Human High–Affinity Receptor for IgG (CD64)", *Blood*, vol. 88 (6), pp. 2358–2360 (1996).

Stewart et al. Clinical Flow Cytometry. Annals of New York Academy of Sciences 677, 94, 1993.

Michon et al. Blood 86: 1124, Aug., 1995.

CYANIDIN COMPOSITIONS AND THERAPEUTIC AND DIAGNOSTIC USES THEREFOR

This application is a divisional application of Ser. No. 08/709,411 filed on Sep. 6, 1996, Pending. The contents of all of the aforementioned application(s) are hereby incorporated by reference.

BACKGROUND OF THE INVENTION

Immunoglobulin G (IgG) Receptors (FcγR)

An IgG antibody molecule has two binding determinants (known as Fab) for its specific cognate antigen, and one binding determinant (Fc) for its cellular receptor (FcγR; reviewed in Ravetch, J. V. and J-P. Kinet 1991, *Ann. Rev. Imm.* 9:457). There are three classes of FcγR, designated FcγRI, FcγRII and FcγRIII. FcγRI has the highest affinity for IgG Fc, and is present on monocytes and macrophages, and on human neutrophils when induced by gamma-interferon (IFN-γ), which also enhances FcγRI expression on monocytes and macrophages (Guyre, P. M. et al., 1983, *J. Clin. Investig.* 72:393). Interleukin-10 (IL-10) is also a potent up-regulator of FcγRI expression on monocytes (Capsoni, F. et al., 1995, *J. Leukoc. Biol.* 58:351). Neutrophil expression of FcγRI is increased almost four-fold by granulocyte-colony stimulating factor (G-CSF; Repp, R. et al., 1991, *Blood* 78:885), and about three-fold during streptococcal pharyngitis (Guyre, P. M. et al., 1990, *J. Clin. Investig.* 86:1892). G-CSF stimulation is associated with enhanced neutrophil-mediated cytotoxicity of tumor cells (Gosselin, E. et al., 1992, *J. Immunol.* 149:3477).

Cellular distribution of the low affinity receptor FcγRII is broader, extending to neutrophils, platelets, B cells, T cell, and possibly mast cells and basophils, in addition to monocytes and macrophages. Human FcγRIII receptors are restricted to macrophages and macrophage cell lines, natural killer (NK) cells, myeloid precursor cells, and a neutrophil cell line (Ravetch and Kinet, supra).

The interaction of antibody-antigen complexes with cells via FcγR triggers a range of responses including antibody-dependent cytotoxicity, degranulation, phagocytosis, and immunomodulatory signals that regulate lymphocyte proliferation and antibody secretion. FcγRI, for example, is active in enhancing antigen presentation (Valerius, T. et al., 1993, *Blood* 82:931) and the FcγRI complementarity designation CD64 has been used to distinguish granulomonocytic progenitor cell populations within a human progenitor cell mixture (CD34$^+$/CD38$^+$; European Patent Application EP O 708 336 A2).

Further, a monoclonal antibody (mAb) that binds FcγRI has been shown to cause down-regulation of expression of this receptor, and administration of this mAb to a chronic immune thrombocytopenia purpura patient resulted in clinical improvement (Ericson, S. G., 1996, *Brit. J. Haematol.* 92:718). The analysis of in vivo function of FcγRI receptors is complicated by the finding that four healthy members of one family lack FcγRI (Ceuppens, J. L., 1988, *J. Clin. Invest.* 82:571). (Cell attaining with PE-Cy5

The tandem dye PE-Cy5 comprises the combination of two fluorescent dyes, R-phycoerythrin (PE) and Cy5.18.OSu (Cy5; Mujumdar, R. B. et al., 1993, *Bioconj. Chem.* 4:105). PE-Cy5 is commonly used conjugated to a monoclonal antibody (mAb), as described in for example, the Jan. 1, 1996, issue of *Blood* that reviews the structure and biology of CD34, accompanied by a cover photograph of a flow cytometric experiment with PE-Cy5 conjugated to an anti-CD34 mAb (Krause D S, et al., 1996, *Blood* 87:1). PE-Cy5 tandem dye is known as "tricolor" since it is frequently used with other dye-mAb conjugates for three-color flow cytometric analyses (Waggoner A S, et al., In: Clinical Flow Cytometry, p.185 (Eds) A. Landay et al. The New York Academy of Sciences, New York, N.Y., 1993).

A non-toxic molecule that binds specifically to FcγRI in vivo would be useful in a variety of diagnostic and therapeutic applications.

SUMMARY OF THE INVENTION

In general the invention relates to agents that specifically bind IgG receptors of the class FcγRI on white blood cells (leukocytes). Because of the functional binding of these compounds, the class of compositions is referred to herein as "GRIL" to indicate an IgG receptor I ligand. The agents are members of the cyanidin family of naturally-occurring plant pigments, exemplified by cyanin, idaein, keracyanin and asterin.

In one aspect, the invention features a class of cyanin compositions of which the fluorescent dye Cy5.18.OSu (referred to as Cy5), and conjugates and derivatives, are examples. The general features of these compositions are firstly functional, which is that they bind with high affinity and specificity to FcγRI IgG receptors found on monocytes and macrophages, and which can also be induced to appear on neutrophils. The second feature is the chemical structure, which may be comprised of at least two moieties, one of which being the cyanin succinimidyl ester composition class. In one embodiment, the second moiety is derived from any of the phycobilisome proteins of which PE is an exemplary but not limiting member.

In another aspect, the present invention features therapeutic compositions comprising a GRIL, for example, a cyanin compound exemplified by a Cy5 reagent, and a therapeutic agent, which therapeutic agent in a preferred embodiment comprises at least one epitope. In one embodiment, the GRIL directs delivery of the useful epitope to FcγRI, and thus comprises a composition which is both vaccine and delivery system. The epitope can be selected from the broad group consisting of a pathogenic organism, a cancer marker, and an allergenic substance. The compounds can thus be used to vaccinate a subject against a pathogenic organism, such as a bacterium, a protozoan, a virus or a fungus. In a preferred embodiment, the epitope for a vaccine is from a Gram positive pathogen, for example, from a cellular or secreted epitope of, *Staphyloccoccus aureus* or *Clostridium tetani*. The invention also features a vaccine against one or more types of cancer, comprising a GRIL and an epitope from a cancer marker which, in a preferred embodiment, is selected from the group consisting of the human EGF receptor family, the mucine TAG72 family, and the carcinoembryonic family.

In another aspect, the present invention features therapeutic compositions comprising a GRIL and a chemotherapeutic cytotoxic anticancer agent, for example, actinomycin D, mitomycin C, adriamycin, taxol, notirimine, or a therapeutic composition comprising a Cy5 reagent and a radionuclide. The therapeutic agent is thus targetted to FcγRI by virtue of the presence of the cyanin, for example a Cy5 or similar reagent, and is useful for treatment of, for example, a myelocytic leukemia, a promyelocytic leukemia or a leukocyte adhesion deficiency.

Methods for targeting FcγRI receptors with a chemotherapeutic or radio-therapeutic GRIL is another aspect of this invention, for the purpose of treating for example, a patient with an autoimmune disease, such as idiopathic thrombocytopenic purpura. Since the agents of the instant invention target IgG receptors, which are located on white blood cells, the methods of the invention include delivery of these compositions ex vivo to cells obtained from a blood sample or a bone marrow sample removed from the patient for such treatment, which blood or bone marrow cell sample or its cellular progeny is subsequently returned to that patient. Further, an interferon, an interleukin or a colony stimulating factor may also be administered to the patient or to the ex vivo blood or bone marrow sample or to cells derived from such samples. In preferred embodiments, the patient is administered IFN-γ, IL-10, or G-CSF.

Another aspect of the invention features compositions and diagnostic methods for detecting and quantifying FcγRI (CD64) in a blood sample or a bone marrow sample from a subject, comprising the steps of contacting the sample with a GRIL stain, removing nonspecifically-bound reagent, illuminating the sample with light of an appropriate excitation wavelength, and detecting the fluorescent cells as an indication of FcγRI-bearing cells in the blood sample. Preferably, at least one additional dye reagent, for example, a fluorescein reagent or a phycoerythrin reagent is used in conjunction with the GRIL. In a preferred embodiment, the GRIL-stained cells are analyzed and isolated by flow cytometry. In another embodiment, the GRIL-stained cells are analyzed by fluorescent microscopy. In these embodiments, the excitation wavelength for illumination is preferably in the range of approximately 475 to 505 nm. Most preferably, the number of FcγRI in blood is an index of the diagnosis, which is measured under appropriate conditions when the detection method is used diagnostically. In a preferred embodiment, the method is used as a diagnostic for leukocyte adhesion deficiency or for a myeloid or promyeloid leukemia; for the presence of infection and/or inflammation; or to monitor therapy during and following administration of a therapeutic agent. The therapeutic agent is preferably an interferon, an interleukin, or a colony stimulating factor, particularly IFN-γ, IL-10, or G-CSF.

In yet another aspect, the invention features a method for screening compounds and identifying among them candidate therapeutic agents which bind to FcγRI. This method comprises contacting a first sample of cells with a candidate agent and contacting a second sample of cells with control buffer, then staining both the first and second samples of cells with a GRIL stain. The samples are illuminated with a wavelength appropriate to cause fluorescence of cells with specifically bound dye, and the fluorescence is used as an index of stained cells, such that an agent which reduces staining of the first sample in comparison to the second sample to a statistically significant extent is a potential therapeutic candidate. The method preferably also comprises a further step of formulating a pharmaceutical preparation of each of the compounds identified by this method as having potential therapeutic activity. This method enables the user to identify low molecular weight drug candidates that interact with IgG receptors. Such drug candidates might be useful in modulation of FcγRI expression, or in preventing Fc binding to FcγRI.

The invention features also a kit for assaying FcγRI on cells, comprising a GRIL stain, a buffer, a container, and instructions for use. This kit is useful for diagnostic purposes. Another kit embodied by the invention is useful for blocking adsorption of cyanidin and Cy5 reagents to FcγRI, comprising an anti-FcγRI antibody, a GRIL stain reagent, a buffer, a container, and instructions for use. This kit would block binding of GRIL reagents to FcγRI, so that such reagents could be used to stain other cell surface molecules.

Other features and advantages of the instant invention will become more apparent form the following detailed description and claims.

BRIEF DESCRIPTION OF THE DRAWINGS

FIG. 1 is a graphic representation of flow cytometric analyses, expressed as mean fluorescence intensity in arbitrary units, of isolated blood cells, U937 cells, and FcR-transfected IIA1.6 cells, each stained with a PE-Cy5-conjugated monoclonal antibody; unstained cells are represented by interrupted lines; each experiment was performed at least five times with monoclonal antibodies, mouse IgG1 isotype, specific for CD4, CD8, CD13, and CD19 conjugates.

DETAILED DESCRIPTION OF THE INVENTION

I. General

Figure 1A:
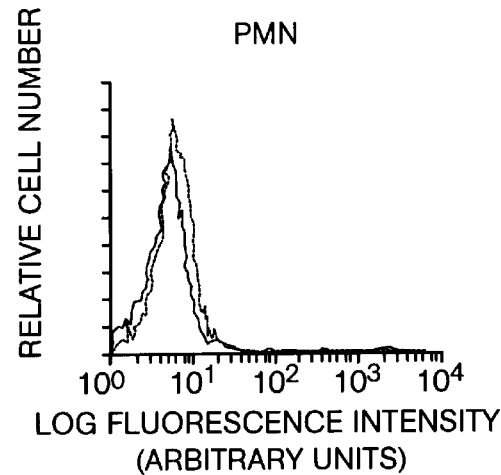
FIG. 1a shows neutrophils (PMNs) isolated from a control donor.

The instant invention pertains to the discovery that particular tandem dye reagents also have the additional property of specific high affinity binding to a class of antibody receptors. Antibodies are elaborated by leukocytes (white blood cells), and are predominantly bound by leukocytes of specific classes. The term "blood" as used herein specifically refers to unfractionated blood, but also to fractions of blood from which some cells may be obtained, for example, to blood samples that have been preserved, or have been treated with anti-clotting agents such as heparin, or to concentrated cellular or bone marrow fractions obtained by centrifugation to concentrate the blood or bone marrow cells. Bone marrow and its cellular components contain blood cell precursors and stem cells that differentiate into mature blood cells.

Many disorders of blood have been characterized, for example, an inherited immune deficiency called leukocyte adhesion deficiency (LAD), and a blood cancer known as acute myeloid leukemia (AML). The inherited gene in LAD affects a β subunit of a ligand receptor which results in defective phagocytic adherence, causing recurrent bacterial and fungal infections. A symptom of LAD is marked leukocytosis (elevation of white blood count up to a range of 30,000–150,000 per cubic millimeter; R. H. Buckley, Primary Immunodeficiency Diseases, p. 1353, 1993. In: Fundamental Immunology, Third Ed., Raven Press, N.Y.; Majima, T. et al., 1990, *J. Immunol* 145:1694). Acute promyelocytic leukemia cells AML-M3 cultured in vitro bind PE-Cy5 stain to a much greater extent than normal cells or cells of other leukemias (Ansari, M. Q. et al., 1995, *Cytometry* 26:83). Similarly, elevation of FcγRI levels has been observed in patients with acute inflammation (Davis B H, et al., 1995, *Lab Hematol* 1:3), using anti-FcγRI monoclonal antibody (mAb) conjugated to fluorescein isothiocyanate (FITC). The methods of the present invention are useful for diagnosis of these conditions, since the GRILs bind specifically to FcγRI on leukocytes, and are more economical and easier to produce and use than monoclonal antibodies.

Further, treatment of subjects with certain agents produces a stimulatory effect on white cell production and increased FcγRI levels, especially cells from patients treated with G-CSF (Repp R, et al., 1991, *Blood* 78:885) or treated with IFN-γ(Guyre P M, et al., 1983, *J. Clin Invest* 72:393). Diagnosis and monitoring of successful therapy, especially of therapeutic protocols that are administered throughout extended periods of time, with these and other agents which stimulate FcγRI are contemplated as applications of the present invention. The diagnostic applications offer the advantages of speed, economy, and patient sample accessibility. The sample required is one or a few drops of blood from a finger prick, and the apparatus necessary is a fluorescence microscope equipped with filters for illumination of slides at one wavelength and for visualization and/or photography at another wavelength. Stains, counterstains, and rinses can be applied during an office or clinic visit, and results obtained within a short period of time.

The present invention contemplates use of the affinity of GRILs for FcγRI to deliver substances specifically to myeloid cells. Cytotoxic substances that are potential anticancer agents can be delivered to myeloid cells by association with or as conjugates of the GRILs of the invention; these substances are exemplified by but not limited to notirimine, actinomycin D, mitomycin C, adriamycin, and taxol. Radionuclides are medically useful for imaging and for therapeutic applications, and are chosen on the basis of the energy spectrum of emission and the half-life of the radionuclide. Preferred radionuclides for delivery to myeloid cells via association with the GRILs include but are not limited to technetium-93m, technetium-95m, technetium-99m, rhenium 186, rhenium 188 and rhenium 189, and iodine-125, and I-131. The term "conjugated" shall mean ionically or covalently attached (i.e. via a cross-linking agent).

A "therapeutic agent" shall mean an agent capable of having a biological effect on a host. Preferred therapeutic agents carry an activity of a vaccine, or are capable of modulating expression of receptors. Therapeutic agents may be conjugated to moieties conferring additional activities including drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense oligonucleotides that bind to a target nucleic acid sequence (e.g. mRNA sequence)), chemotherapeutic nucleotides, peptides, non-specific (non-antibody) proteins, boron containing compound (e.g. carborane), photodynamic agents (e.g. rhodamine 123), enediynes (e.g. calicheamicins, esperamicins, dynemicin, neocarzinostatin chromophore, and kedarcidin chromophore) and transcription based pharmaceuticals.

The term "cancer markers" refers to antigens that are specifically associated with surfaces of particular types of cancer cells. Many forms of cancer can be characterized by production of proteins associated with that form of the disease, and are not found in normal tissue. Often these proteins are used at a specific stage of embryonic development, and are not observed during normal adult lifetime. These markers are particularly useful in the design of therapeutic agents against cancer, for example, as a source of epitopes for anti-cancer vaccines. The instant invention comprises delivery of cancer-specific epitopes to FcγRI by association of the appropriate epitope with a GRIL. Examples of tumor markers that are envisioned as a source of epitopes in the present invention include breast and ovarian cancers, which are sex hormone dependent cancers. Breast tumors may be characterized by abnormally expressed receptors, e.g. those of the human-EGF-like receptor family (HER), for example HER-2, -3, and 4. The invention is not limited to these embodiments of HER antigens. Additional examples of sex hormone-dependent cancer include prostate cancer (Smith, P., 1995, *Cancer Surveys Vol. 23: Preventing Prostate Cancer*, Imper. Cancer Research Fund and testicular cancers). The nestin protein, which is expressed by neuroepithelial stem cells during normal mammalian fetal development, is also expressed on tumors of the central nervous system, including most forms of brain cancer (McKay, D. G. Ronald, U.S. Pat. No. 5,338,839, Aug. 16, 1994). It is also expressed on melanomas found on the skin and on those which have metastasized to other tissues (V. A. Florenes, R. Holm, O. Myklebost, U. Lendahl, O. Fodstad, 1994, *Cancer Res*. 54: 354–6) and are hence difficult to detect and treat.

Other tumor types for which the methods of this invention are exemplified by, but are not limited to, Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840), gastrointestinal cancer (R. Fishel et al., International Application WO 95/14085, May 26, 1995), cancers characterized by development of multiple drug resistance during chemotherapy (J. M. Croop et al., U.S. Pat. No. 5,198,344), and cancers characterized by the presence of at least one of a large number of oncogenes well known to the skilled artisan, such as Rb, ras, and c-myc, the sequences of which are available for analysis to those with skill in the art. Tumors which express a mucine antigen, such as TAG72, are also suitable sources of epitopes to be incorporated into dye reagents for delivery as vaccines, as are tumors which express at least one of the carcinoembryonic antigen (CEA) family of proteins. The CEA gene family consists of more than 17 closely related genes belonging to the immunoglobulin gene superfamily. The antibodies recognizing this family of antigens are identified based on their reactivity with transfectants from 5 subgroups of the CEA superfamily. These are a-BGP, b-CGM6, c-NCA, d-CGM1 and e-CEA (DAKO catalog, anti-CD66abce).

Antigens are also associated with the surfaces or secretion products of micro-organisms. The term "pathogen" is meant to include organisms that cause disorders, such disorders produced by one or more particular species of bacteria, viruses, fungi, and protozoans which are disease-producing organisms. In this invention, pathogens are exemplified, but not limited to, Gram-negative bacterial species such as Escherichia coli serotype 0157:H7, *Helicobacter pylori, H. mustelae, Haemophilus influenzae and H. ducreyi, Pseudomonas aeruginosa, Shigella dysenteria, Salmonella typhi and S. paratyphi*; Gram-positive bacterial species such as Mycobacterium tuberculosis, M. leprae, *Clostridium tetani, Staphylococcus aureus*, and *Streptococcus hemolyticus*; obligate intracellular bacterial organisms such as Rickettsia and Chlamydia species; retroviruses, which are RNA containing viruses that use reverse transcriptase to synthesize complementary DNA, including but not limited to HIV-1, and -2; other pathogenic viruses such HSV-I and -II, non-A non-B non-C hepatitis virus, pox viruses, and rabies viruses; fungi such as Candida and Aspergillus species;

protozoa such as *Cryptosporidium parvum, Entamoeba histolytica* and *Giardia lamblia*; and animal pathogens such as Newcastle disease virus. Obtaining unique epitopes from these organisms by screening proteins and by assaying peptides in vitro are commonly known to those skilled in the art; many examples have been described and the appropriate amino acid residue sequence may be accessed from GenBank.

The term "infection" is meant to include persistence and growth of a pathogen in a subject host. While symptoms used to diagnose the presence of infection include fever, inflammation, pain, joint and muscular sensations at or near sites of infection, the absence of one or more of these symptoms do not preclude infection in a subject host organism. The term "inflammation" indicates a set of host reactions that accompany infection, and may also be present in the absence of infection, for example, as a symptom of autoimmune reactions, degenerative diseases, tissue remodeling disorders, exposure to allergens, and/or other conditions. Inflammatory responses include cellular processes such as neutrophil, mast cell and basophil degranulation with associated release of proteases, histamines, and superoxide generation, and production of and responses to cytokines such as interferons and tumor necrosis factor. Acute inflammation is associated with increased staining of leukocytes with FITC-labelled anti-CD64 mAb, due to elevated CD64 expression (Davis, B H et al., supra).

II. Fluorescent Dyes

The compositions, methods and kits of the instant invention pertain to dyes, dye reagents, and tandem dye reagents for fluorescence applications, the invention comprising that certain of these dyes and reagents bind with high affinity and specificity to a class of receptors for IgG antibodies known as FcγRI. Tandem dye reagents are comprised of two or more covalently linked individual dye moieties, such that light of a particular wavelength or range of wavelengths is absorbed by one moiety of the molecule, which undergoes a molecular excitation and then emits light at a different wavelength (the property of fluorescence). Light emitted by this first moiety is substantially absorbed by a second moiety of the tandem, which in turn emits light at another wavelength. These properties have proved tandem dyes useful for identification of cell types and locations of subcellular structure, using antibody conjugates of a number of fluorescent dyes.

Light spectra properties for some commonly used single and tandem fluorescent dyes are shown in Table 1 (reproduced in modified form from the Immunotech-Coulter Corp. catalog, "Cytometry Monoclonal Reagent Guide," 8/95, p.3). The parameters of peaks of maximal light absorbance, excitation and emission enable the concurrent use of two or more fluorescent dyes in a single experiment or analysis (see, for example, Chang, T. W., 1993, U.S. Pat. No. 5,256,542).

Tandem fluorescent dye antibody conjugates are used for cell separation applications (Loken, M. R. et al., 1992, U.S. Pat. No. 5,137,809) and for cell analysis, and are used in combination with one or more "simple" fluorescent dyes such as fluorescein isothiocyanate (FITC) and/or phycoerythrin (R-PE or PE; Kronick, M., 1986, *J. Immunol. Methods* 92:1; and U.S. Pat. No. 4,857,474, Aug. 15, 1989) comprised of a single dye moiety conjugated to an antibody of different specificity. Thus each dye species is conjugated to an antibody specific for a different subcellular component or molecule. Usefulness of a dye in combination with others is determined by two aspects of spectra of light energy interactions: (1) the extent to which a dye molecule is excited by a single illumination wavelength or narrow band of wavelengths, such as PE-Texas Red and PE-Cy5 listed below in Table 1 each of which can be used with FITC and PE; and (2) the extent to which each excited dye molecule emits light of wavelength sufficiently different from the other dyes so as to be discernible as a unique color or peak. The first aspect enables the user to illuminate the multiply-stained biological sample with a single wavelength, 488 nm in the this example, and the second aspect enables the user to observe and record different colors of emission, each of which is associated with a particular cell type or a structure.

TABLE 1

Examples of Fluorochromes

| Fluorochrome | Maximum Absorbance | Excitation at 488 nm | Maximum Emission | Fluorescence |
|---|---|---|---|---|
| Fluorescein isothiocyanate (FITC) | 495 nm | Yes | 525 nm | Green |
| Phycoerythrin (PE) | 488; 565 nm | Yes | 575 nm | Orange-red |
| Energy Coupled Dye [ECD] (PE-Texas-Red) | 488; 565 nm | Yes | 610–635 nm | Red |
| Phycoerythrin-Cyanin 5 (PE-Cy5) | 488; 565; 652 nm | Yes | 670 nm | Deep-red |

Preferred methods of observation and analysis include direct visualization with a microscope fitted with a light source and filters appropriate to the excitation and emission wavelengths, and use of a camera attached to the microscope. A most preferred method of the invention for cell separation and enumeration of live cells appropriately stained with this class of dye reagents, is isolation by use of a flow cytometry apparatus such as a FACScan or a FACStar (Becton Dickinson, San Jose, Calif.). This instrument illuminates a mixed cell population, for example at 488 nm with an argon laser source of light, and uses an emission spectrum signal from each cell detected in a moving fluid such as a buffer, to sort each cell as it is flowing past the detector using a variety of bandpass filters for collection of emitted light (see, for example, Lohmeyer, J. et al., 1994, *J. Immunol. Methods* 172:59). The apparatus can count and collect cell populations yielding both data and cell fractions for further analysis and use.

Flow cytometry has been used extensively to separate different classes of cells in the cell populations in blood and in bone marrow; it has been particularly useful to separate the different types of leukocytes from each other, as a tool in typing of leukemias and lymphomas (Howard, M. et al, 1994, *J. Clin. Path.* (London) 47:1006; U.S. Pat. No. 5,234, 816), and to obtain blood stem cell progenitor fractions isolated away from other cell types U.S. Pat. No. 5,137,809, Aug. 11, 1992), for research and for therapeutic uses. Flow cytometers have become routine in clinical laboratory use. Several parameters of a cell may be measured simultaneously: forward scattered light is used to measure cell size; and a second scatter detector provides information on the granularity of the cell cytoplasm, used to differentiate the various types of leukocytes. Fluorescent light emitted from the fluorescent dye "fluorochromes," each of which is bound to a specific monoclonal antibody, is collected by the cytometer. These parameters create a broad range of applications dependent on the specificity and combination of monoclonal antibody-dye conjugates used.

A number of reagents are available comprising antibodies conjugated to FITC, the isothiocyanate of fluorescein (3',6'-dihydroxyspiro[isobenzofuran-1(3H),9'-[9H]xanthen]-3-one; Merck Index, 11th Edition, 1989, Merck and Co., Rahway, N.J.). FITC is a fluorochrome with a molecular weight of 389 kDa and an absorption maximum at 495 nm. Its excitation by 488-nm light leads to a fluorescence emission maximum around 520 nm. Using a 530+/−15 nm bandpass (BP) filter will give optimum detection for this fluorochrome. FITC has a high quantum yield (efficiency of energy transfer from absorption to emission fluorescence) and approximately half of the absorbed photons are emitted as fluorescent light. The number of FITC molecules per conjugate partner (antibody, avidin, or streptavidin, for example) is usually in the range of three to five molecules. The disodium salt of fluorescein is used diagnostically in cases of corneal trauma, intraocular inflammation and for ophthalmic angiography and contact lens fitting.

Another fluorescent dye component of numerous antibody conjugate reagents, PE is an accessory photosynthetic pigment found in red algae, which functions in vivo to transfer light energy to chlorophyll during photosynthesis. The 240 kDA protein has 34 phycoerythrobilin fluorochromes, each a linear tetrapyrrole, per molecule, which when excited by 488-nm light, emit light at a 576 nm peak. For single-laser flow cytometer use, a 585+/−21 nm BP filter is used for optimal detection. When performing multi-color analysis with a dual-laser system, a tighter window of detection is required to compensate for the other conjugates being used, for example a 575+/−13 nm BP filter. Conjugation chemistry for PharMingen (San Diego, Calif.) PE products yields an average of one PE molecule per antibody or other protein.

Cyanin was isolated from cornflower (*Centaurea cyanus*), and is structurally the 3,5-diglucoside of cyanidin, which is 2-(3,4-dihydroxyphenyl)- 3,5,7-trihydroxy-1-benzopyrylium chloride and was isolated from banana (Merck Index, supra). Another cyanidin derivative, the 3-rhamnoglucoside isolated from sour cherries, is described as having therapeutic application for night blindness. Anthocyanosides of bilberry (*Vaccinium myrtillus*) fruit are marketed as nutraceutical food supplements, which according to one manufacturer (Amrion, Inc., Boulder, Colo.), are consumed orally to improve vasodilation, decrease capillary permeability, protect collagen in blood vessels, operate as antioxidants and support control of the inflammatory process, improving general vision, stomach linings, blood-brain barrier and the veins of the legs and colon (*Gen. Engin. News* 16 (11), p.27, 1996).

The cyanidin derivative dye Cy5, also designated Cy5.18.OSu, has the chemical structure 5,5'-bis-sulfo-1,1'-(ε-carboxyphenyl)-3,3,3', 3'-tetramethylindodicarbocyanin- disuccinimidyl ester (A. S. Waggoner et al., In: Clinical Flow Cytometry, p.185 (Eds) A. Landay et al. The New York Academy of Sciences, New York, N.Y., 1993). Cyanin dye labeling reagents for sulfhydryl groups (Ernst, L. A. et al., 1989, *Cytometry* 10:3) and carboxymethylindocyanin succinimidyl esters (Southwick, P. L. et al., 1990, *Cytometry* 11:418) have been described, and compositions claimed in patent applications U.S. Pat. No. 4,981,977 and 5,268,486), the contents of which patents and publications are herein incorporated by reference. Structure of Cy5, and its synthesis and spectra for absorption and emission of light are given in Mujumdar, R. B., 1993, *Bioconj. Chem.* 4:105. Cy5 is described as a sulfoindocyanin succinimidyl ester, which are amino-reactive cyanin dyes that contain a negatively charged sulfonate group on the aromatic nucleus of the indocyanin fluorophore. The Cy5 members of this family are characterized by a 5-carbon, unsaturated polymethine bridge connecting two substituted ring structures. Cy5 can be excited with a 633 nm HeNe laser line or a 647 nm line of a Dr laser. Cy5 and its derivatives are noted for photostability, which is comparable to or better than that of fluorescein. The extinction coefficient (L/mol cm) of 250, 000 is very high. Related dyes (Mujumdar et al., supra), with similar structures and modes of synthesis are here encompassed within the expression "Cy5" so that this expression encompasses sulfoindocyanin succinimidyl esters of cyanin dye labeling reagents in general, for example, Cy3.29.OSu (known as Cy3) and Cy7.18.OH. The terms Cy5 reagent, Cy5 conjugate and Cy5 derivatives shall mean a conjugate comprising at least a Cy5 moiety and another molecular entity. Additional new derivatives of this basic structure have been described, the sulfobenzindocyanin succinimidyl esters of cyanin reagents (Mujumdar, S. R. et al., 1996, *Bioconj. Chem* 7:356), which share properties of Cy5 and other sulfoindocyanin succinimidyl esters, and are contemplated to bind FcγRI with affinity and specificity.

Use of the Cy5 reagent PE-Cy5, comprised of Cy5 in tandem with PE, to provide three-color fluorescence by excitation with a single 488 nm argon ion laser line is described in Waggoner et al., 1993, supra, as are conditions for optimization. Major problems with tandem dyes based on Texas Red are attributed to instability of one moiety, resulting during use in leakage of emission into the spectrum of the other moiety, limiting the ability to use Texas Red dyes emitting light at or near the wavelength of that second moiety. Cy5 and its reagent family of dyes, however, emit light at longer wavelengths than Texas Red, so that analysis of data obtained from using Cy5 with other dyes requires minimal channel compensation in setting detection windows and in downstream calculations. Considerations for best mode use of Cy5 reagents include the process of synthesis of the Cy5 reagent from the components, since the ratio of number of Cy5 molecules bound per molecule of conjugate affects the relative emission wavelength spectrum of the synthesis product. Thus for PE-Cy5, the efficiency of energy transfer from PE to Cy5 increases as more Cy5 molecules are bound to each PE up to an optimal range, beyond which quenching interactions among excess Cy5 moieties is observed. The optimum ratio is 4 to 8 Cy5 per PE in the PE-Cy5 tandem dye (Waggoner et al., 1993, supra). Tandem dyes are light sensitive, and stability during usage is improved if dyes are stored and handled and experiments are performed under dark conditions, as indicated in the Examples, infra.

The improved signal size due to extent of fluorescence and absence of background for PE-Cy5, compared to that of previously synthesized tandem dyes, make it a successful analytical tool for cell analysis studies with antibody-dye conjugates. However at least one report of "non-specific" binding of a variety of PE-Cy5 products from different suppliers to myeloid cells has been reported (Stewart S J, et al., supra), attributed to the Cy5 moiety because PE-Texas Red conjugates do not exhibit this property. In contrast, Takizawa et al. report binding of PE and its mAb conjugates to low affinity mouse IgG receptors FcγRII and FcγRIII (*J. Immunol. Methods*, 1993, 162:269).

The instant invention defines an unexpected, intrinsic specific binding affinity of Cy5 reagents, for example, Cy5, PE-Cy5 and antibody conjugates and related reagents, and provides methods for use of these for flow cytometry and for diagnostic, screening and therapeutic applications, as described in the Examples below. The term "PE-Cy5" as used here designates the specific tandem dye comprised of phycoerythrin and Cy5.18.OSu; the term "PE-Cy5 reagent" designates, for example but not limited to, PE-Cy5 conjugates to antibodies, to genetically engineered binding proteins and peptides U.S. Pat. No. 5,233,409 and 5,403,484), to avidin, to biotin, or to other molecular entities.

In general, the present invention contemplates engineering a useful specific ligand for FcγRI comprised of two moieties, one of which being a dye of the cyanin succinimidyl ester composition class. This specific ligand for FcγRI shall be designated "GRIL" to indicate an IgG receptor I ligand. The precise light absorption, excitation and emission spectra of the GRIL of the present invention, while useful for some applications here such as diagnostics, is not an essential property for the high affinity and specificity required for other applications, such as therapeutics. If the GRIL field of use for application requires fluorescent staining, the GRIL shall be designated "GRIL stain," or "GRIL dye," and cells dyed with such compositions are noted as "GRIL-stained cells." Further, GRIL novel compositions comprised of a phycobilisome moiety and a cyanin succinimidyl ester moiety, said tandem dye additionally substituted with for example, an antibody, binding protein, avidin, or other substitutent, are designated herein as "GRIL compositions" or "GRIL reagents."

III. Antibodies and Antibody Receptors.

Receptors for IgG molecules are known as FcγR, of which FcγRI is a high affinity receptor found on monocytes and macrophages, and are inducible on neutrophils and eosinophils (Van de Winkel J G I, et al., 1993, *Immunol Today* 14:215). The lower affinity IgG receptors are FcγRII, found on neutrophils (polymorphonuclear neutrophils, PMNs), monocytes, and platelets, and FcγRIII, found on macrophages, PMNs, and natural killer cells (NKs). The low affinity IgG receptors are also found on mast cells and subsets of T cells (Ravetch et al., 1991, *Ann. Rev. Imm.* 9:457). Biological functions associated with binding of IgG to these receptors include phagocytosis, superoxide generation, cytotoxicity, and triggering mediator release. The biological role of FcγRI has not been fully determined, since because of its high affinity it might be saturated with IgG in vivo, suggesting a steady state situation. Data including induction of expression of FcγRI during streptococcal infection (Guyre, P. M et al., 1990, *J. Clin. Invest.* 86:1892), induction during IFN-γ treatment of patients with chronic granulomatous disease, and on neutrophils from a neglible quantity in healthy individuals to a large number during acute inflammation (Davis, B H et al., supra) suggest an important role in resistance to infection (Van de Winkel J G I, et al, 1993, *Immunol Today* 14; 215).

Antibodies are proteins synthesized by the immune cells of higher animals in response to a unit of recognition of a foreign molecule, known as an epitope. Populations of antibody molecules typically found circulating in higher animals are known as "polyclonal" because the population comprises a large set of antibodies each of which is specific for one of the many differing epitopes found in the population of immunogens to which that animal has been exposed, each antibody of which is characterized by a specific affinity for its cognate epitope. An epitope is the smallest determinant of antigenicity, which for a protein, comprises a peptide of six to eight residues in length (Berzofsky, J. and I. Berkower, (1993) in Paul, W., Ed., *Fundamental Immunology*, Raven Press, N.Y., p.246). The affinity of an antibody molecule for its cognate epitope ranges from low, e.g. $10^{-6}$ M, to high, e.g., $10^{-11}$ M.

The term "monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (*Nature*, 1975, 256:495–497; see also Brown et al., 1981, *J. Immunol* 127:539–46; Brown et al. 1980, *J. Biol Chem* 255:4980–83; Yeh et al., 1976, *PNAS* 76:2927–31; and Yeh et al., 1982, *Int. J. Cancer* 29:269–75) and the more recent human B cell hybridoma technique (Kozbor et al., 1983, *Immunol Today* 4:72), EBV-hybridoma technique (Cole et al., 1985, Monoclonal Antibodies and Cancer Therapy, Alan R. Liss, Inc., pp. 77–96), and trioma techniques.

Immune response to "foreign" antigens comprises the notion that "self" proteins and other molecules expressed within an organism are not antigenic or immunogenic to that organism. In fact, discrimination between isologous or homologous determinants and "foreign," or heterologous determinants is achieved through maturation of the immune system of an organism during development of the immune system. A system of selection against immune cells bearing antibodies with binding determinants to "self" occurs, so that when mature the immune system does not attack proteins or other molecules native to the organism. In certain pathological conditions known as "autoimmune diseases," however, such discrimination is not as accurate, and endogenous structures may be subject to attack from the immune system. Examples of autoimmune diseases and conditions in which there is autoimmune exacerbation of symptoms include systemic lupus erythematosus, myasthemia gravis, multiple sclerosis, and rheumatoid arthritis. One autoimmune disease, idiopathic thrombocytopenic purpura (ITP), which affects approximately 150,000 patients in the United States (according to the U.S. Department of HHS, 1992 data), results from macrophages in the spleen and liver removing autoantibody-coated platelets from circulation. The autoantibodies generally have the IgG isotype (Schwarz, R. S., Autoimmunity and Autoimmune Diseases, 1993, p. 1075. In: Fundamental Immunology, 3rd Ed., W. E. Paul, Ed., Raven Press, N.Y.), and the disease results in continuous platelet destruction. Classes of compositions of the instant invention are capable of binding to a site on the FcγRI receptor, by virtue of comprising a binding determinant for a site on this receptor. Invented compositions can thereby also modulate the number of these receptors on the cell surface, and can further bind to the functional portion of these receptors and compete with antibody binding, and accordingly are potential agents for treatment of autoimmune diseases. Further, amino acid residue sequence data of the Fv regions of the antibody binding determinant is the basis for obtaining a three-dimensional model of the features of the protein such as size, charge, and shape of the set of residues which comprise this binding site, so that the portion of the agents which bind to the receptor can be synthesized, and drugs which mimic this binding site may be designed.

One type of antigen can be an allergen. An "allergen" refers to a substance that can induce an allergic or asthmatic response in a susceptible subject. The number of allergens that elicit a sensitive response in a proportion of a population is enormous, and includes pollens, insect venoms, animal dander, dust mite proteins, fungal spores and drugs (e.g. penicillin). Examples of natural animal and plant allergens include proteins specific to the following genera: Felis (*Felis domesticus*); Canis (*Canis familiaris*); Dermatophagoides (e.g. *Dermatophagoides farinae*); Periplaneta (e.g. *Periplaneta americana*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

IV. Pharmaceutical Compositions

The compounds of the invention can be incorporated into pharmaceutical compositions suitable for administration to a subject in vivo. In a preferred embodiment, the pharmaceutical composition comprises a GRIL, a GRIL composition or reagent of the invention and a pharmaceutically acceptable carrier. In yet another embodiment of the present invention, the pharmaceutical composition can be administered by combination therapy, i.e., combined with other agents. For example, the combination therapy can include a composition of the present invention with at least one anti-cancer agent, one antibiotic, one vaccine, or other conventional therapy.

Further, the cells of a tissue, e.g. blood or bone marrow, may be removed from a patient, fractionated and cultured if appropriate to expand the cell number, treated ex vivo with the GRIL, for example, a Cy5 reagent, in a pharmaceutically acceptable carrier, and returned to the patient for therapy. During the ex vivo culture and expansion, a particular cell type may be selected, e.g. a monocyte or neutrophil population or stem cells of such leukocytes. Further, ex vivo cultured cells may be treated at various points during ex vivo culture and expansion, with agents to modify certain functional FcγR molecules. Agents include but are not limited to, growth factors, cytokines, lymphokines such as IFN-γ, G-CSF, tumor necrosis factor (TNF), granulocyte macrophage- colony stimulating factor (GM-CSF), and interleukins such as IL-2, IL-10 and IL-12. Preferred agents of the instant invention include IFN-γ, G-CSF, and IL-10.

As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

A "pharmaceutically acceptable salt" refers to a salt that retains the desired biological activity of the parent compound and does not impart any undesired toxicological effects (see e.g., Berge, S. M., et al., 1977, *J. Pharm. Sci.* 66:1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained* and *Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984, *J. Neuroimmunol.* 7:27). Except insofar as any conventional media or agent is incompatible with the active compound, use thereof in the pharmaceutical compositions of the invention is contemplated.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Generally, out of one hundred per cent, this amount will range from about 0.01 per cent to about ninety-nine percent of active ingredient, preferably from about 0.1 per cent to about 70 per cent, most preferably from about 1 per cent to about 30 per cent. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Transdermal patches offer the advantage of providing controlled delivery of a compound of the present therapeutic inventions to the body. Absorption enhancers can also be used to increase the flux of the composition across the skin. The rate of such flux can be controlled by either providing a rate controlling membrane or dispersing the composition in a polymer matrix or gel. Devices, including patches, which transdermally deliver a composition by iontophoresis or other electrically-assisted methods can also be employed in the present invention, including, for example, the devices described in U.S. Pat. Nos. 4,708,716 and 5,372,579.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

When the active compound is suitably protected, as described above, the compound may be orally administered, for example, with an inert diluent or an assimilable edible carrier. As used herein "pharmaceutically acceptable carrier" includes any and all solvents, dispersion media, liposome formulations and coatings, antibacterial and antifungal agents, isotonic and absorption delaying agents, and other discussed above. The use of such media and agents for formulation of pharmaceutically active substances that are stable to oral administration is well known in the art. Except insofar as any conventional media or agent is incompatible with the active compound, use thereof in the therapeutic compositions is contemplated.

The invention is further illustrated by the following examples, which should not be construed as further limiting. The contents of all references, pending patent applications and published patents, cited throughout this application, are hereby expressly incorporated by reference.

EXAMPLES

The following methodology described in the Materials and Methods section was used throughout these Examples, set forth below.

Materials and Methods

Immunohematology protocols for use with dye-antibody conjugates, with unconjugated tandem-dye, or other reagents obtained from Immunotech/Coulter Corporation (Westbrook, M E and Kennesaw, G A), are described here. For immunofluorescence staining of a cell suspension of human peripheral blood, cells were prepared and enriched as follows. If samples had a normal or high white cell count, whole blood was used, and the red cells were eliminated by lysis. For samples with a low white cell count, the red blood cells were separated by the Ficoll Hypaque (Pharmacia-Upjohn, Piscataway, N.J.) method as follows. To a cell suspension of blood collected in EDTA anticoagulant, an equal volume of NaCl (0.9%) was added. The diluted blood was pipetted down the side of a conical centrifuge tube containing a volume of Ficoll Hypaque equal to about half that of the blood, and the tube was centrifuged 700 g for 15 minutes at room temperature. The mononucleated cells at the plasma interface were removed with a Pasteur Pipette, washed three times with a volume of Hank's or similar solution equivalent to the volume of collected mononucleated cells, and centrifuged at 300 g for 10 minutes at 4° C. after each wash. The supernatant was aspirated and discarded after each wash, and the cells were resuspended in suspension medium to a concentration of approximately $10^6$ cells/ml, mixed gently, and cell viability determined using Trypan Blue or ethidium bromide (cells were about 80% viable).

The direct staining method uses a primary antibody that has been directly conjugated to a fluorochrome. For separated cells, the cell suspension (100 μl) was pipetted into each of 2 tubes (one of which serves as a control for autofluorescence). Conjugated dye-monoclonal antibody (20 μl) was added to one test tube which was mixed gently. Cells were incubated for 30 minutes at 4° C. in the dark, washed twice with PBS or Hank's medium, and resuspended in 100 to 500 μl of fixative reagent or 1% formaldehyde prior to analysis with flow cytometry or fluorescence microscopy. For fluorescence microscopy, a drop of mounting medium (70% glycerol, 30% glycine buffer pH 8.6) was manually added.

For immunostaining with whole blood in the case of high white count (greater than 10,000 cells/ml), blood was diluted in isotonic solution to obtain approximately 5,000 leukocytes/ml (normal value). Whole blood, 100 μl, was pipetted into a test tube, and 20 μl of dye-conjugated monoclonal antibody solution was added to the test tube and the contents were mixed gently and incubated for 75 minutes at room temperature in the dark. Lysing solution was then added, and incubation continued for 5 minutes at 25° C. in the dark. Fixative reagent was added, cells were centrifuged 5 minutes at 700 g, resuspended in 100 μl to 500 μl of PBS or 1% formaldehyde, and analyzed by flow cytometry or fluorescence microscopy, respectively. For fluorescence microscopy, a drop of mounting medium was added.

For double labelling, the primary incubation of cells was performed with a mixture of antibodies, each conjugated to a different fluorochrome. The combination described here is FITC/phycoerythrin; the same procedure is suitable for staining with a combination of FITC- and PE-Cy5-conjugated antibodies. For immunostaining of separated cells, 100 μl of cell suspension was pipette into each of 2 tubes (one of which serves as control). Monoclonal antibodies solution, 20 μl, was added to the test tube and 20 μl of saline to the control tube, and tubes were mixed gently and incubated for 30 minutes at 4° C. Cells were washed twice with phosphate-buffered saline (PBS) or Hank's medium, resuspended in 100 to 500 μl of PBS or saline containing 0.5% formaldehyde, and analyzed with flow cytometry or fluorescence microscopy. For fluorescence microscopy, a drop of mounting medium was added.

To analyze immunofluorescence with a sample of whole blood, 100 μl of blood treated with EDTA was pipetted into 2 tubes (one control tube and one test tube), and 20 μl of conjugated monoclonal antibodies solution was added to the test tube, and 20 μl of PBS into the control tube, then 180 μl of PBS was added to each tube and the contents mixed gently. Tubes were incubated 15 minutes at room temperature, lysing solution was added, and incubations continued 5 minutes at 25° C. in the dark. Fixative reagent was added, cells were centrifuged 3 minutes at 400 g, washed twice with PBS, and resuspended in 100 μl to 500 μl of PBS or formaldehyde (1%) for analysis with flow cytometry or fluorescence microscopy, respectively. For fluorescence microscopy, a drop of mounting medium (70% glycerol, 30% glycine buffer pH 8.8) was added.

Immunohematology protocols for use with dye-antibody conjugates, with unconjugated tandem-dye, or other reagents obtained from DAKO Corp. (Carpinteria, Calif. and Glostrup, Denmark), are described here. Venous blood was collected into a test tube containing an anticoagulant, and mononuclear cells were isolated by centrifugation on a separation medium. Alternatively, red cells were lysed after the antibody-dye incubation procedure. Mononuclear cells were washed twice with RPMI 1640 (Gibco/BRL, Bethesda, Md.) or PBS, pH 7.2–7.4. Cell suspensions containing up to $1 \times 10^8$ cells in 100 μl were mixed with up to 10 μl antibody-conjugated dye and incubated in the dark at 4° C. for 30 minutes. (Double-antibody and triple-antibody labelling conjugates were also used with this protocol). Cells were washed twice with PBS containing 2% bovine serum albumin, and resuspended in an appropriate fluid for flow cytometry analysis. These same procedures, with double-antibody or triple-antibody staining are also useful for evaluating immature myelopoiesis in peripheral blood and in bone marrow.

Immunohematology protocol for use with dye-antibody conjugates, with unconjugated tandem-dye, or other reagents obtained from PharMingen (San Diego, Calif.) is described here. Cells were harvested from tissue, and a single cell suspension was prepared. Red blood cells were removed by lysis or density gradient. Cells were washed once in cold wash buffer (PBS/0.1% $NaN_3$/1.0% fetal bovine serum and centrifuged at 350×g for 5 minutes. Cell pellets were resuspended to a concentration of $2×10^7$ cells/ml (i.e., $10^6$ cells per 50 $\mu$l). Primary mAbs (e.g., fluorochrome-conjugated mAbs) were diluted to predetermined optimal concentrations in wash buffer and delivered to the wells of a U-bottom microtiter plate in volumes of 50 $\mu$l. Cells ($10^6$) were delivered in 50 $\mu$l to each well containing 50 $\mu$l of mAb (or 50 $\mu$l wash buffer for negative controls), and mixed by gently vortexing or tapping. Plates were incubated at 4° C. for 20–40 minutes in the dark centrifuged 350 g for 5 minutes, and washed twice with 200 $\mu$l wash buffer (or three times if a biotin-conjugated primary antibody is used). After each centrifugation, wells were aspirated or plates were flicked to remove supernatant. Vortexing gently or tapping plates was used to loosen pellets prior to addition of the next wash or diluted secondary reagent. If a second-step reagent was needed, cell pellets were resuspended in 100 $\mu$l of appropriate secondary reagent (e.g., fluorochrome-conjugated avidin, streptavidin, anti-Ig allotype, anti-Ig isotype, polyclonal anti-Ig). For example, antibody was diluted to one $\mu$l per 100 $\mu$l in wash buffer and added to each well containing loosened cell pellet, and plates were incubated at 4° C. for 20 to 40 minutes in the dark. Cells were washed twice with 200 $\mu$l wash buffer. Wash buffer (100 $\mu$l) was used to transfer cell pellets to 0.4 ml aliquots of wash buffer (final concentration approximately $10^6$ cells in 0.5 ml) in tubes appropriate for flow cytometry. Sample data on flow cytometer were acquired as soon as possible after staining.

Example 1. Binding of PE-Cy5 monoclonal antibody conjugates to human PMNs and neutrophils, and effect of G-CSF treatment.

The specific binding of PE-Cy5 to Fc$\gamma$RI was observed by examining properties of 14 different PE-Cy5 conjugated monoclonal antibodies by flow cytometry. These conjugates were produced by three different companies (DAKO, Gertrup, Denmark and Carpenteria, Calif.; Immunotech, Brussels, Belgium and Westbrook, Me., and as a division of Coulter, Miami, Fla.; and PharMingen, San Diego, Calif.), and were used according to methodology recommended by the suppliers, described supra.

Figure 1B:
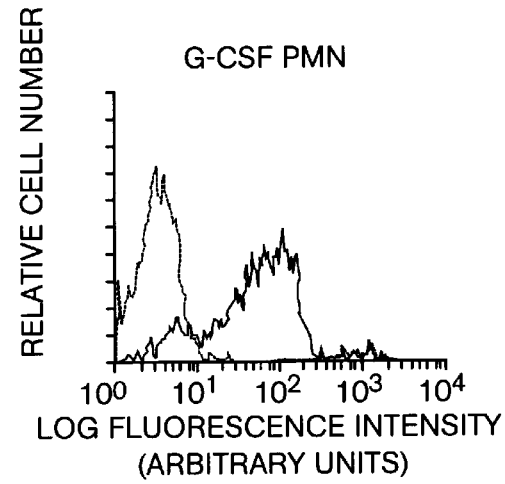
FIG. 1b shows PMNs isolated from a patient treated with G-CSF for 4 days.
Figure 1C:
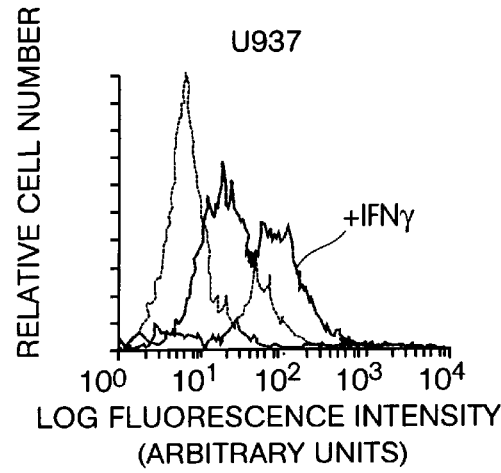
FIG. 1c shows U937 monocytoid cells cultured in RPMI 1640 medium/ 10% FCS or upon overnight culture in PRMI 1640 medium with 300 U/ml IFN-γ as indicated.
Figure 1D:
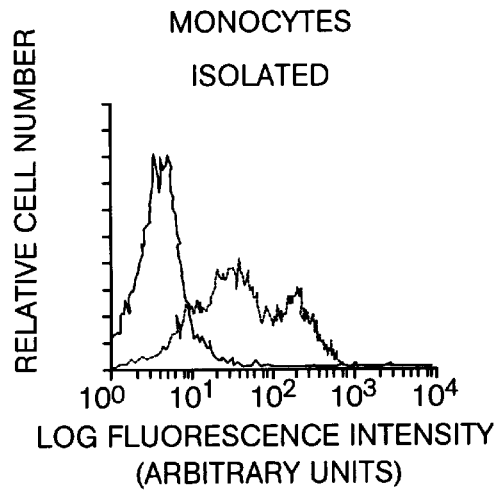
FIG. 1d shows monocytes stained upon isolation.

Staining of isolated monocytes and neutrophils (PMN) from normal donors, and PMN from patients treated with G-CSF in vivo, were analyzed. Surprisingly, both monocytes (FIG. 1d) and G-CSF-PMN (FIG. 1b) exhibited bright staining using a PE-Cy5 reagent comprised of this tandem dye conjugated to mAb directed to T and B cell antigens. Fluorescence of cells, in arbitrary units, was found to be one to two orders of magnitude greater than background, in contrast to fluorescence of normal PMN (FIG. 1a). PMN express high levels of Fc$\gamma$RIII (CD16), whereas monocytes and G-CSF-treated PMN, in addition to Fc$\gamma$RIII, express Fc$\gamma$RI (Van de Winkel J G I, et al., 1993, *Immunol Today* 14:215; Repp R, et al., 1991, *Blood* 78:885). The observed "non-specific" PE-Cy5 reagent staining pattern previously found by others, among different cell types, was thus observed here to correlate with cells that show Fc$\gamma$RI expression.

Example 2. The effect of gamma-interferon (IFN-$\gamma$) treatment on binding of PE-Cy5 monoclonal antibody conjugates to PMNs and U93 7 monocytoid cells.

Binding of PE-Cy5 conjugates to PMN and U937 human monocytoid cells cultured overnight with IFN-$\gamma$, a condition known to increase Fc$\gamma$RI expression levels (Guyre P M, et al., 1983, *J. Clin Invest* 72:393), was assessed. The data with both PMN and U937 cells show that binding of PE-Cy5 antibody conjugates was enhanced by treatment with IFN-y (U937 shown in FIG. 1c). Since IFN-$\gamma$ induces Fc$\gamma$RI on PMN and increases expression of this receptor on monocytes and macrophages, this result shows that PE-Cy5 binding correlates with presence and extent of expression of Fc$\gamma$RI on myeloid cells.

Figure 1E:
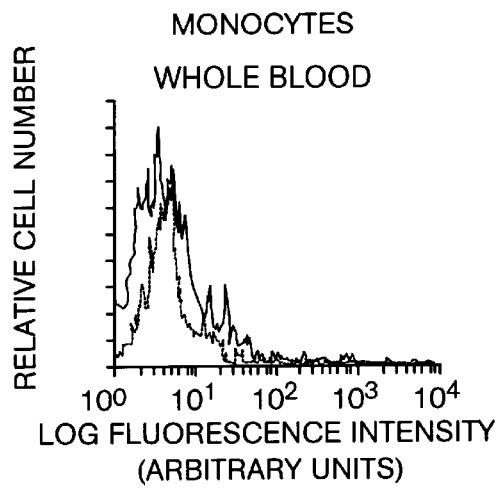
FIG. 1e shows monocytes in whole blood following lysis of red cells, which were gated from mononuclear cell fractions by flow cytometry based on FITC-labeled CD14 monoclonal antibody.
Figure 1F:
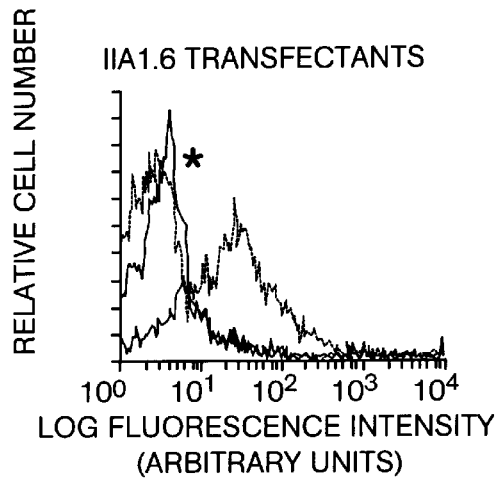
FIG. 1f shows murine B IIA1.6 cell transfectants with human FcγRIIa, human FcγRIIb, human FcαR (marked by *), or human FcγRI.

Example 3. Transfection and PE-Cy5 conjugate binding of mouse IIA1.6B cells with genes encoding Fc$\gamma$RI, Fc$\gamma$RIIa, Fc$\gamma$RIIb, or Fc$\alpha$R To assess the specificity of binding of PE-Cy5 conjugates to Fc$\gamma$RI, a series of FcR-transfectants, each transfectant engineered to express one FcR molecular type, was tested. Recipient IIA1.6 cells mouse B cells are devoid of IgG receptors; samples were transfected with each of the genes encoding the different human Fc receptors for IgG (Fc$\gamma$RI, CD64; Van Vugt M J, et al., 1996, *Blood* 87:3593; Fc$\gamma$RIIa, CD32; Fc$\gamma$RIIb1, CD32, Van den Herik-Oudijk I E, et al., 1995, Blood 85:2202) and for IgA receptor Fc$\alpha$R, CD89 (Morton H C, et al., 1995, *J. Biol Chem* 270:29781) derived from the A20 B cell lymphoma (Morton, H C, et al., supra). Transfectants were stained with different PE-Cy5 mAb conjugates (covalently linked to antibodies to CD3, CD4, or CD8). Only cells transfected with Fc$\gamma$RI exhibited binding of the PE-Cy5 conjugates (FIG. 1f), since the fluorescence intensity of other transfectants (Fc$\gamma$RII, Fc$\gamma$RIII, or Fc$\alpha$R) was identical to cells lacking Fc$\gamma$RI.

Similar data were obtained here with Fc$\gamma$RI-transfected mouse 3T3 cells see also (Van Vugt M J, et al., 1996, *Blood* 87:3593). Specific staining to Fc$\gamma$RI-bearing cells was not seen with FITC-labeled or PE-labeled mAb, which shows that Fc$\gamma$RI interacts with a site in the Cy5 moiety of the PE-Cy5 tandem fluorochrome exclusively among these dyes. Mouse Fc$\gamma$RII and Fc$\gamma$RIII but not Fc$\gamma$RI bind PE dye and PE dye conjugates (Takizawa, F. et al., supra). Unconjugated PE dye was observed here not to bind to human IgG receptors (data not shown). Further, mouse Fc$\gamma$RI but not Fc$\gamma$RII and Fc$\gamma$RIII binds specifically to the PE-Cy5 tandem dye antibody conjugates, which is the same pattern seen with human receptors.

Example 4. Binding of non-conjugated Cy5 dye to mouse IIA1.6B cells transfected with the gene for Fc$\gamma$RI.

The Examples above show that PE-Cy5 and antibody conjugates of this tandem dye bind specifically to human Fc$\gamma$RI, however binding of Fc$\gamma$RI was not observed with unconjugated PE. To determine the binding specificity of unconjugated Cy5 reactive dye (DAKO), this reagent was dissolved in DMSO at a concentration of 10 mg/ml, and diluted in 0.05 Tris-HCl, 0.1 M NaCl, 15 mM $NaN_3$, 1% BSA to a stock concentration of 1 mg/ml. Further, unconjugated PE-Cy5 was used in the same series of experiments, diluted in PBS to a stock concentration of 1.5 mg/ml.

Untransfected IIA1.6 B-cells and these cells transfected with the gene for human Fc$\gamma$RI (see references, supra), $2×10^5$ cells in 20 $\mu$l per test, were stained for one hour at 4° C. with 10 $\mu$l Cy5. Successful staining of the transfectants, but not the control cells, was observed at concentrations of dye that ranged from 100 ng/ml to 1 g/ml. Mean fluorescent intensity of transfectants was at least an order of magnitude greater than for the control cells. Staining of cells with PE-Cy5 was also observed with transfectants, but not control cells, at dye concentrations that ranged from 30 ng/ml to 1.5 $\mu$g/ml. All fluorescence experiments were performed using band filter gates for excitation and emission wavelengths appropriate for PE-Cy5 described supra, so that diminished activity for Cy5 in comparison with PE and PE-Cy5 is due to comparatively low absorption by Cy5 at 488 nm. In spite of this suboptimal excitation, the data show that Cy5, and the Cy5 portion of Cy5 tandem dye derivatives bind with specificity to FcγRI.

Example 5. Blocking PE-Cy5 antibody conjugate binding to FcγRI for use of PE-Cy5 reagents to cognate conjugate ligands.

PE-Cy5 staining of FcγRI-expressing cells was blocked to an extent greater than 90%, by treating cells with either 20% human pooled serum, or with a monoclonal CD64 antibody blocking the FcγRI-ligand-binding region (mAb 197, Van de Winkel J G J, et al., 1993, *Immunol Today* 14:215), or with aggregated IgG. Exemplary data (FIG. 1e) show PE-Cy5 conjugate staining of monocytes reduced by greater than 80% in whole blood staining assays.

"Non-specific" staining of macrophages has been observed (Stewart S J, et al., supra) and "sensitive and specific staining" of AML-FAB M3 leukemic cells was also observed (Ansari M O, et al., 1996, *Cytometry* 26:813) using PE-Cy5 conjugated mAb. Those results are shown by the data of the present invention to be due to specific high affinity binding by the PE-Cy5 reagents to FcγRI that are present on macrophages, and that are expressed on AML leukemic cells.

The data of the present invention show that Cy5 reagents can be used to monitor the course of therapeutic treatments with IFN-γ or G-CSF, and as diagnostics, in lieu of more complicated and expensive reagents.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for detecting FcγRI (CD64) in a biological sample from a subject, comprising the steps of:
    a) contacting the sample with a cyanin compound, Cy5, in the absence of other compounds that bind FcγRI;
    b) illuminating the sample with light of an appropriate excitation wavelength for Cy5; and
    c) detecting fluorescence.

2. The method of claim 1, wherein the Cy5 further comprises an additional dye reagent.

3. The method of claim 2, wherein the additional dye reagent is a fluorescein reagent or a phycoerythrin reagent.

4. The method of claim 1, wherein the step of detecting fluorescence is done by flow cytometry.

5. The method of claim 1, wherein the step of detecting fluorescence is done by fluorescent microscopy.

6. The method of claim 1, wherein the excitation wavelength is approximately 475 to 505 nm.

7. The method of claim 1, wherein the sample is obtained from a human subject.

8. The method of claim 1, wherein the level of fluorescence of the sample, is compared to the level of fluorescence of a second biological sample from a different subject.

9. The method of claim 1, wherein a therapeutic agent is administered to the subject prior to the step of detecting.

10. The method of claim 9, wherein the therapeutic agent is selected from the group consisting of an interferon, an interleukin, and a colony stimulating factor.

11. The method of claim 10, wherein the interferon is IFN-γ.

12. The method of claim 10, wherein the interleukin is IL-10.

13. The method of claim 10, wherein the colony stimulating factor is G-CSF.

14. The method of claim 1, further comprising the step of removing unbound Cy5 before illuminating the sample with light of an appropriate excitation wavelength.

* * * * *